United States Patent [19]

Schendel et al.

[11] Patent Number: 5,243,039

[45] Date of Patent: Sep. 7, 1993

[54] BACILLUS MGA3 ASPARTOKINASE II GENE

[75] Inventors: Frederick J. Schendel, Oakdale; Michael C. Flickinger, St. Paul, both of Minn.

[73] Assignee: Regents of the University of Minnesota, Minneapolis, Minn.

[21] Appl. No.: 684,135

[22] Filed: Apr. 12, 1991

Related U.S. Application Data

[63] Continuation-in-part of Ser. No. 673,263, Mar. 20, 1991, abandoned, which is a continuation of Ser. No. 351,436, May 12, 1989, abandoned, said Ser. No. 673,263, Continuation-in-part of Ser. No. 673,264, is a continuation of Ser. No. 335,691, Apr. 10, 1989, abandoned.

[51] Int. Cl.$^5$ .............. C07H 21/04; C12N 9/12; C12N 15/54; C12N 15/75
[52] U.S. Cl. .................. 536/23.2; 435/193; 435/194; 435/252.3
[58] Field of Search .......... 435/193, 200, 252.5, 435/852, 194, 115, 252.3; 536/27, 23.2; 935/18

[56] References Cited

U.S. PATENT DOCUMENTS 3,707,441 12/1972 Shiio et al. ............. 195/29
4,652,527 3/1987 Stirling .................. 435/253

OTHER PUBLICATIONS

Guettler, M. et al. (1988) ASM Abstract 1-95, p. 196.
Chen, N. Y. et al. *J. Biol. Chem.* 263(19):9526-9532 (1988).
Schendel, F. J. et al. *Appl. and Environ. Micro.* 56(4):963-970 (1990).
L. Graves et al., *J. Bacteriol.*, 172, 218 (1990).
D. Moir et al., *J. Biol. Chem.*, 252, 4648 (1977).
R. Bondaryk et al., *J. Biol. Chem.*, 260, 592 (1985).
N.-Y. Chen et al., *J. Biol. Chem.*, 262, 8787 (1987).
N. Al-Awadhi et al., *Biotechnol. Bioeng.*, 36, 816 (1990).
H. Hagino et al., *Biotechnol. Lett.*, 3, 425 (1981).
R. Yasbin et al., *J. Bacteriol.*, 121, 296 (1975).

F. Sanger et al., *Proc. Natl. Acad. Sci. USA*, 74, 5463 (1977).
H. Shimotsu et al., *J. Bacteriol.*, 166, 461 (1986).
M. Hitchcock et al., *Biochim. Biophys. Acta*, 445, 350 (1976).
U. Laemmli, *Nature*, 227, 680 (1970).
J.-J. Zhang et al., *J. Bacteriol.*, 172, 701 (1990).
J. Theze et al., *J. Bacteriol.*, 117, 133 (1974).
M. Cassan et al., *J. Biol. Chem.*, 261, 1052 (1986).
M. Katinka et al., *Proc. Natl. Acad. Sci. USA*, 77, 5730 (1980).
J. Rafalski et al., *J. Biol. Chem.*, 263, 2146 (1988).
M. Zakin et al., *J. Biol. Chem.*, 258, 3028 (1983).
G. Lee et al., *Mol. Gen. Genet.*, 180, 57 (1980).
L. Band et al., *DNA*, 3, 17 (1984).
C. Moran, Jr. et al., *Mol. Gen. Genet.*, 186, 339 (1982).
J.-C. Patte et al., *Biochim. Biophys. Acta*, 136, 245 (1967).
R. Kolter et al., *Ann. Rev. Genet.*, 16, 113 (1982).
T. Kunkel, *Proc. Natl. Acad. Sci. USA*, 82, 488 (1985).
C. Wolff et al., *J. Bacteriol.*, 170, 4509 (1988).
T. Akiba et al., *J. Ferment. Technol.*, 48, 323 (1970).
N. Al-Awadhi et al., *Appl. Microbiol. Biotechnol.*, 29, 485 (1988).
P. Andrews, *Biochem. J.*, 91, 222 (1964).
C. Anthony, *Biochemistry of Methylotrophs*, Academic Press, London, p. 3 (1982).
H. Birnboim et al., *Nucl. Acids Res.*, 7, 1513 (1979).
A. Brooke et al., *Arch. Microbiology*, 151, 268 (1989).
R. Cox et al., *Biochem. J.*, 141, 605 (1974).

(List continued on next page.)

*Primary Examiner*—Robert A. Wax
*Assistant Examiner*—Dian Cook
*Attorney, Agent, or Firm*—Merchant, Gould, Smith, Edell, Welter & Schmidt

[57] ABSTRACT

The present invention provides the isolated DNA sequence encoding the αB dimer subunit of the lysine-sensitive aspartokinase II isozyme from the thermophilic methylotrophic Bacillus sp. MGA3.

2 Claims, 6 Drawing Sheets

OTHER PUBLICATIONS

G. de Vries, *FEMS Microbiology Reviews*, 39, 235 (1986).

G. de Vries et al., *FEMS Microbiology Review*, 75, 57 (1990).

L. Dijkhuizen et al., *FEMS Microbiology Letters*, 52, 209 (1988).

C. Haber et al., *Science*, 221, 1147 (1983).

R. Hanson, *Adv. Applied Microbiology*, 26, 3 (1980).

N. Harms et al., *J. Bacteriology*, 169, 3969 (1987).

B. Holloway, *Methylotrophs: Microbiology, Biochemistry and Genetics*, C. T. Hou, ed., CRC Press, Boca Raton, Fla., pp. 1–39 (1984).

B. Holloway et al., in *Microbial Growth on $C_1$ Compounds*, H. W. Van Verseveld and J. A. Duine, eds., Martinies Nyhoff, Dordrecht, pp. 223–229 (1987).

P. Large et al., *Methylotrophy and Biotechnology. Longman Scientific and Technical*, John Wiley and Sons, New York, pp. 146–162 (1988).

J. Linton et al., in *Microbial Growth on $C_1$ Compounds*, H. W. Van Verseveld and J. A. Duine, eds., Martinies Nyhoff, Dordrecht, pp. 263–271 (1987).

A. Mimura et al., *J. Ferment. Technol.*, 56, 243 (1978).

F. Schendel et al., *1989 ASM Annual Meeting* (Poster Session).

I. Shiio, *Biotechnology of Amino Acid Production*, K. Aida, I. Chibata, K. Nakayama, K. Takinami, and H. Yamada, eds., pp. 188–206 (1983).

B. Snedecor et al., *Applied Microbiology*, 27, 1112 (1974).

O. Tosaka et al., *Biotechnology of Amino Acid Production*, K. Aida, I. Chibata, K. Nakayama, K. Takinami, and H. Yamada, eds., pp. 152–172 (1983).

O. Tosaka et al., *Trends in Biotechnology*, 1, 70 (1983).

R. Whittenbury et al., *J. General Microbiology*, 61, 219 (1970).

F. Schendel et al., *1990 ASM Annual Meeting* (Poster Session).

```
     S   L   L   A   M   A   L   N   E   K   G   Y   E   A   I   S   Y   T   G   W   Q   A   G      101
    ATT ACA ACT GAA CCT AAA GTT TTT GGG AAC GCG AGA ATA TTC CAA AAT ATC GAA ACC GAA ATT CAA AAA CAG   1035
     I   T   T   E   P   K   V   F   G   N   A   R   I   F   Q   N   I   E   T   E   I   Q   K   Q   124
    CTA AAC GAA GGA AAA GTA GTT GTA ATT GGT GCC TTC CAA AAT GGT ATT GAT GAG CAC GGA GAA CAC ACG ACT   1104
     L   N   E   G   K   V   V   V   I   G   A   F   Q   N   G   I   D   E   H   G   E   H   T   T   147
    CTT GGG AGA GGC GGA TCC TCC ACT GTT ACG GCA GCG GCT GCT GCC AAG AAA TGT GAT   1173
     L   G   R   G   G   S   S   T   V   T   A   A   A   A   A   K   K   C   D   T                   170
    ATT TAC ACC GAT GTT GAT ACT GGA GTT TTT ACT TAT CCG AGG TCG AGA AAG CTT GCT   1242
     I   Y   T   D   V   D   T   G   V   F   T   Y   P   R   S   R   K   L   A                       193
    TCT ATT TCA TAT GAT GAA ATG CTT GCA AAT CCG GGC GTC CAT CCA GAA GAA GCA GTA   1311
     S   I   S   Y   D   E   M   L   A   N   P   G   V   H   P   E   E   A   V                       216
    GAA TTT GCG AAA GTA ATG TAC GGA ATT GAG GTG CGC AGT ATG CGA GAA GGG ACG ATC   1380
     E   F   A   K   V   M   Y   G   I   E   V   R   S   M   R   E   G   T   I                       239
    ATT GAG GAG GAA GTA ACA ATG CAA GAA ATT ACT GTC GTT GCT TTT GAT GAT GAA ATC ACT   1449
     I   E   E   E   V   T   M   Q   E   I   T   V   V   A   F   D   D   E   I   T                   262
    CGA GTA ACA TTT GGA CCA TTG AAC TCA ACG TTA AGT ACT ATT ACA ACG CTT GCT CAA   1518
     R   V   T   F   G   P   L   N   S   T   L   S   T   I   T   T   L   A   Q
```

FIG. 2C

```
     E   L   S   G   S   A   V   K   S   E   R   *                                                411
     CCA TAA GGT CCT GGC TCG CGT TTG CAG TTA CTA AAT ATT GTA GAA ACA GTA ATC ATG TTT TTT AAT ATT  2001
     TAG TTT CTG AGA GTG GGC CCT TCT TAG TGG CTT AGC GTC TAT CCA TAA ATC ATG GCT TTA CGA CGT      2070
     CTT TTT TGT CCC ACT TAA CCG TTA TCT TTA GCA CTT ATC CCT TTT TAC GAG GGT GTT CAA ACG CTT CAG  2139
     CAA TTA CTT TTT GCT GTT CGT CAA TTT GCT GGG CAA TAA ATC CCG CCA ACT GAA AAG AGA TAT CTT      2208
     TTT TTG ACT GCA GGT                                                                          2223
              └Pst I┘
```

FIG. 2D

FIG. 3A    V GLIVQKFGGT...    PREDICTED
           GLIVQKFG           OBSERVED

FIG. 3B    MEQNLVVRGVA...     PREDICTED
           MEQNLVVR           OBSERVED

BACILLUS MGA3 ASPARTOKINASE II GENE

CROSS-REFERENCE TO RELATED APPLICATION

This application is a continuation-in-part of U.S. patent application Ser. No. 07/673,263, filed Mar. 20, 1991, now abandoned, which is a continuation of U.S. patent application Ser. No. 07/351,436, filed May 12, 1989, now abandoned. U.S. patent application Ser. No. 07/673,263 is in turn a continuation-in-part of U.S. patent application Ser. No. 07/673,264, filed Mar. 20, 1991, which is a continuation of U.S. patent application Ser. No. 07/335,691, filed Apr. 10, 1989, now abandoned.

BACKGROUND OF THE INVENTION

Aspartokinase (ATP:4-L-Aspartate-4-phosphotransferase [EC 2.7.2.4]) catalyses the conversion of aspartate and ATP to 4-phosphoaspartate and ADP. As shown in FIG. 1 for *E. coli*, aspartokinase is the first enzyme utilized in the biosynthetic pathway leading to lysine, threonine, and methionine. The biosynthesis of these nutritionally important amino acids is highly regulated. One mechanism for the regulation of this pathway is via the production of several isozymes of aspartokinase having different repressors and allosteric inhibitors. In both *Escherichia coli* and recently in *Bacillus subtilis*, three isozymes of aspartokinase differing in their sensitivity to repression and inhibition by lysine, threonine, methionine, and diaminopimelate have been identified. The three *B. subtilis* isozymes are feedback-inhibited by diaminopimelate, lysine, or threonine plus lysine, respectively (L. M. Graves, *J. Bacteriol.*, 172, 218 (1990)). The lysine-sensitive aspartokinase II from *B. subtilis* has been purified to homogeneity by D. Moir et al., *J. Biol. Chem.*, 252, 4648 (1977). The gene encoding this enzyme has also been cloned and sequenced, as reported by R. P. Bondaryk et al., *J. Biol. Chem.*, 260, 592 (1985) and N. Y. Chen et al., *J. Biol. Chem.*, 262, 8787 (1987).

Recently, F. J. Schendel et al. in *J. Appl. Environ. Microbiol.*, 56, 963 (1990), identified homoserine auxotrophs and S-(2-aminoethyl)-cysteine (AEC) resistant mutants of a thermophilic methylotrophic Bacillus sp. which overproduce significant quantities of L-lysine at 50° C. Such thermophilic methylotrophs may have advantages over other organisms for industrial use, as discussed by Al-Awadhi et al., *Biotechnol. Bioeng.*, 36, 816, 821 (1990). In particular, the methylotrophic Bacillus MGA3 identified by F. J. Schendel et al., cited supra, may have significant advantages over other bacilli for the overproduction of lysine since it does not sporulate at high temperatures even under conditions of nutrient limitation, in contrast to lysine-producing mutants of *B. licheniformis* that sporulated when grown at temperatures greater than 40° C. (H. Hagino et al., *Biotechnol. Lett.*, 3, 425 (1981)).

Since both spore components, diaminopimelate and dipicolinic acid, are derived from the lysine biosynthetic pathway, as shown in FIG. 1, differences in the regulation of this pathway may occur between this thermophilic Bacillus sp. and other mesophilic bacilli. Therefore, a need exists to isolate and characterize the informational macromolecules (DNA and RNA) which function in the biosynthetic pathway to lysine, methionine and threonine in the thermotolerant Bacillus sp. MGA3. A further need exists to isolate and characterize the products, such as the enzymes, that function in these biosynthetic pathways. A further need exists to produce mutant varieties of said informational macromolecules, in order to improve the properties of the enzymes and other polypeptides encoded thereby, or to produce improved strains of thermotolerant, methylotrophic bacteria.

SUMMARY OF THE INVENTION

The present invention provides a DNA sequence in substantially pure form, which corresponds to the structural gene coding for the $\alpha$B dimer subunit of lysinesensitive aspartokinase II (AKII) of the methylotrophic thermotolerant Bacillus sp. MGA3. The native form of this enzyme is an $\alpha_2 B_2$ tetramer. The DNA sequence was identified by cloning the structural gene from a genomic library via complementation of an *Escherichia coli* auxotrophic mutant lacking all three aspartokinase isozymes. The nucleotide sequence of the entire 2.2 Kb PstI fragment has been determined to be as depicted in FIG. 2 and a single open reading frame coding for the aspartokinase II enzyme was identified at positions 664–1885 of this fragment.

The present invention also provides a substantially pure enzyme corresponding to this form of aspartokinase II (AKII) and a substantially pure polypeptide corresponding to the $\alpha$B dimer subunit of AKII. AKII is an $\alpha_2\beta_2$ tetramer ($M_r$ 122,000) with the $\beta$ subunit ($M_r$ 18,000) being encoded within the $\alpha$ subunit ($M_r$ 45,000) in the same reading frame. The N-terminal sequence of both the $\alpha$ and $\beta$ subunit were found to be identical with those predicted from the gene sequence. The predicted AKII sequence of 411 amino acids is only 76% identical with the sequence of the *B. subtilis* aspartokinase II. The transcription initiation site of the AKII gene is located approximately 350 base pairs upstream of the translation start site, and putative promoter regions at $-10$ (TATGCT) and $-35$ (ATGACA) were also identified. Therefore, this gene represents a significant point of divergence of the MGA3 lysine biosynthetic pathway from the pathway operative in other mesophilic bacilli.

Availability of the MGA3 AKII gene, coupled with knowledge of its sequence, permits the production of mutant forms of the present AKII, via mutagenesis of the gene. Mutant forms of the MGA3 AKII gene may be useful to produce microorganisms such as new strains of bacteria, which overproduce lysine at higher levels, or under even more stringent environmental conditions. Methodologies for the mutagenesis of the MGA3 AKII gene are discussed in detail hereinbelow.

As used herein, with respect to an enzyme or a subunit thereof, the term "corresponding to aspartokinase II (AKII)" is intended to mean that the enzyme or the subunit referred to exhibits substantial sequence homology to AKII derived from MGA3 (e.g., $\geq 85$–$90\%$) and that the enzyme also exhibits a substantially equivalent profile of bioactivity, e.g., exhibits $\geq 85$–$90\%$ of the lysine sensitivity exhibited by AKII from MGA3.

As used herein, with respect to a DNA sequence which encodes AKII or a subunit thereof, the term "substantially pure" means that the DNA sequence is free of other DNA sequences that occur naturally in MGA3, e.g., that it has been isolated from MGA3, via the methodologies of recombinant DNA technology, as described herein, or has bee prepared by known techniques of organic synthesis. Likewise, as used with respect to an AKII enzyme or a subunit thereof, the term "substantially pure" means that the enzyme is free of the other components of naturally occurring Bacillus, in that it has been isolated from a biological medium or has been prepared by known techniques organic synthesis or of recombinant DNA technology.

All the patents, patent documents and publications cited herein are incorporated by reference herein.

BRIEF DESCRIPTION OF THE DRAWINGS

FIGS. 2A-2D depict the nucleotide sequence of the 2.2 Kb PstI fragment of the genomic clone pAA8671 (Sequence I.D. No. 1) and the derived amino acid sequence for Bacillus MGA3 aspartokinase II αβ dimer subunit (Sequence I.D. No. 2). Regions of dyad symmetry are overlined with arrows, potential ribosome binding sites are underlined, the −10 and −35 regions of the putative promoter are boxed, and the transcription initiation site is marked with an asterisk.

FIGS. 3A and 3B are a comparison of the predicted and determined N-terminal amino acid sequences for (a) the α subunit, and (b) the β subunit of AK-II from B. MGA3.

DETAILED DESCRIPTION OF THE INVENTION

Figure 1:
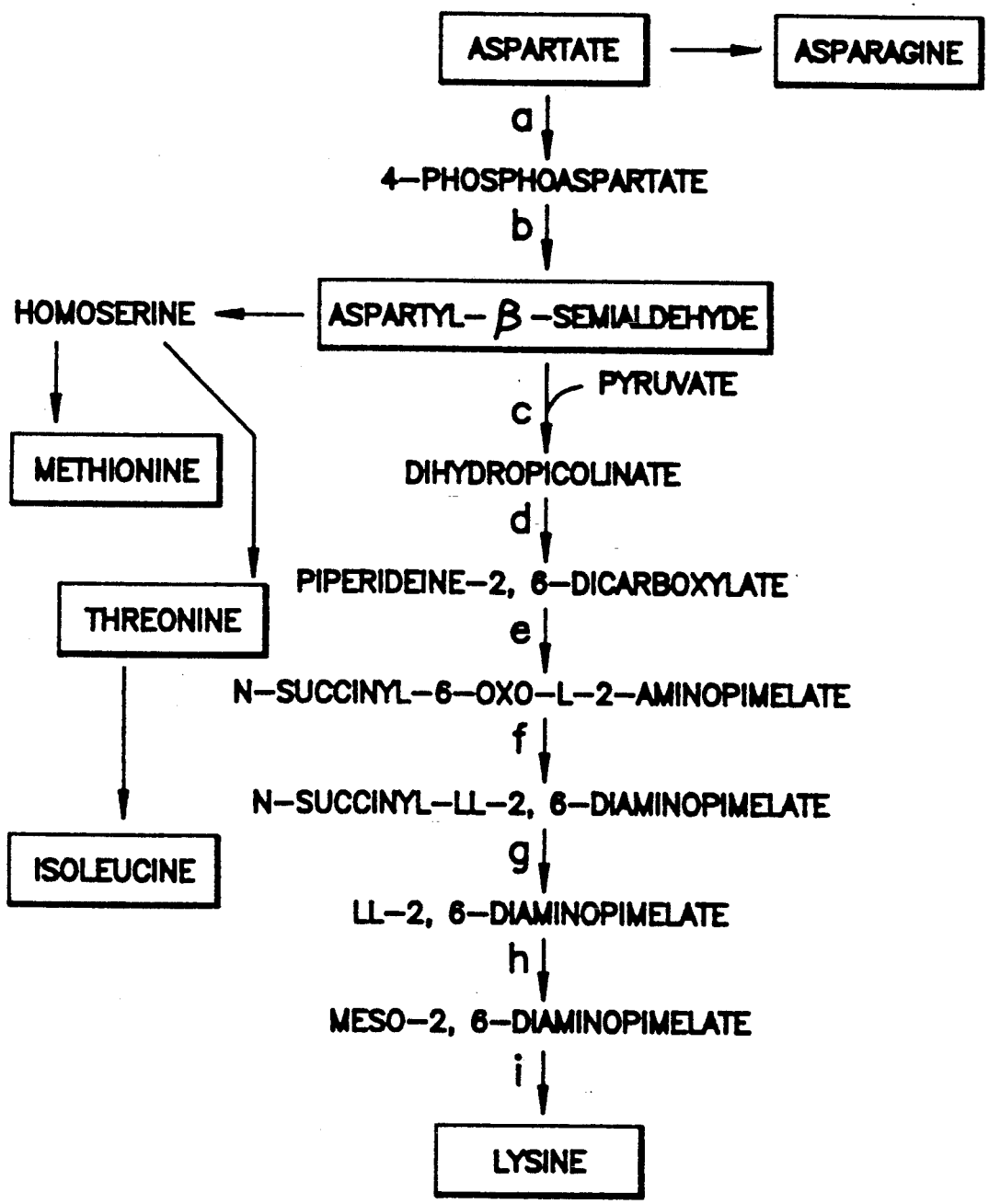
FIG. 1 is a schematic depiction of the lysine biosynthetic pathway in *E. coli* wherein the following letters indicate the following enzymes: a—aspartokinase; b—aspartylsemialdehyde dehydrogenase; c—dihydrodipicolinic acid synthase; d—dihydrodipicolinic acid reductase; e—succinyloxoaminopimelate synthase; f—succinyldiaminopimelate amino transferase; g—succinyldiaminopimelate desuccinylase; h—diaminopimelate racemase; and i—mesodiaminopimelate decarboxylase.

The invention will be described by reference to the following detailed examples, wherein the bacterial strains, vectors and recombinant plasmids used are summarized in Table 1, below.

mented with 50 μg/ml of the appropriate amino acid. Bacillus MGA3 (ATCC 53907, American Type Culture Collection, Rockville, Md., USA) was grown at 53° C. in baffled flasks rotated at 350 rpm on MY medium (F. J. Schendel et al., cited supra) containing 1% methanol. Solid media contained 15 g of agar (Sigma, St. Louis, Mo.) per liter of medium. Selective media contained antibiotics at the following concentrations: 15 μg tetracycline per ml, 35 μg chloramphenicol per ml, 100 μg ampicillin per ml, and 50 μg streptomycin sulfate per ml.

B. Recombinant Genetic Methods

DNA manipulations were carried out according to T. Maniatis et al. (cited supra) unless otherwise stated. Transformations of *E. coli* strains DH5αF' and GM2163 were carried out according to D. Hanahan (cited supra). Electrotransformation of *E. coli* strain Gif106M1 was carried out using a Gene Pulser apparatus (Bio-Rad Lab; Richmond, Calif.) at 12.5 KV per cm and 25 μFD capacitance. Cells were allowed to recover for one hour in SOC medium before plating. Electrocompetent *E. coli* Gif106M1 cells were prepared by growth in SOC to mid-log phase. One liter of cells were harvested by centrifugation at 7,000×g, washed twice with an equal volume of cold sterile water, and resuspended in 40 ml cold 10% glycerol. The cells were harvested by centrifugation, resuspended in 2 ml cold 10% glycerol, and 150 μl samples frozen in a dry-ice ethanol bath. The cells were then stored at −80° C. until needed. Restriction endonucleases, T4 DNA ligase, AMV reverse transcriptase, and bacterial alkaline phosphatase were purchased from Bethesda Research Labs (Gaithersburg, Md.) and used according to the instructions of the supplier. Bacillus MGA3 chromosomal DNA was isolated from cells grown in MY medium using the method of R. E. Yasbin et al., *J. Bacteriol.*, 121, 269 (1975).

C. DNA Sequencing and Analysis

TABLE 1

Bacterial Strains and Plasmids

| Strain | Relevant Markers | Reference or Source |
|---|---|---|
| *Escherichia coli* | | |
| DH5αF' | F'φ80dlacZΔM15 Δ(lacZYA-argF)U169 recA1 end A1 hsdR17(r$_K$−, m$_K$+) supE44λ−thi-1 gyrA relA1 | Bethesda Research Lab |
| Gif106M1 | F− thrA1101 supE44 λ− rpsL9 malT1(λ$^R$) xyl-7 mtl-2 ilvA296 metL1000 arg-1000 thi-1 lysC1001 | Barbra Bachman |
| Bacillus | | |
| MGA3 | — | ATCC 53907 |
| MGA3 S-12 | Hse− | R. S. Hanson |
| Plasmids | | |
| pUC19cm | Cm$^r$ | J. Fuchs |
| pBR322 | Tc$^r$, Ap$^r$ | F. Bolivar et al.[b] |
| pAA8363 | Tc$^r$, AK$^{+a}$ | This study |
| pAA8671 | Cm$^r$, AK$^+$ | This study |
| pAA8802 | Cm$^r$, AK$^−$ | This study |

[a]AK, Aspartokinase activity.
[b]F. Bolivar et al., Gene, 2, 95 (1977).

A. Media and Growth Conditions

Strains of *E. coli* were grown at 37° C. in baffled Erlenmeyer flasks (Bellco) rotated at 280-320 rpm (Labline) on SOC medium (D. Hanahan, "Techniques for transformation of *E. coli*," in *DNA Cloning: A Practical Approach*, D. M. Glover, ed., IRL Press, Washington, D.C. (1985) at pages 109-135), or M9 medium (T. Maniatis et al., *Molecular Cloning: A Laboratory Manual*, Cold Spring Harbor Laboratory, Cold Spring Harbor, N.Y. (1982)). Auxotrophic stains were imple- Nested deletions were constructed by unidirectional exonuclease III-S1 nuclease digestion (Erase-a-base, Promega Corp., Madison, Wis.). The DNA sequence was determined by the dideoxy-chain termination method of F. Sanger et al., *PNAS USA*, 74, 5463 (1977) for both strands using Sequenase (United States Biochemicals, Cleveland, Ohio). Analysis of the DNA sequence data was carried out using Intellagenetics software (University of Minnesota Molecular Biology Computing Center).

D. Primer Extension

Total RNA was isolated and primer extension was performed as described by F. M. Ausubel et al., in *Current Protocols in Molecular Biology*, John Wiley & Sons, N.Y. (1987). For the isolation of RNA, *E. coli* was grown in SOC and B. MGA3 was grown in minimal methanol media (F. S. Schendel et al., cited supra). Total RNA was isolated from *E. coli* as described by F. M. Ausubel et al., cited supra, and from B. MGA3 as described by H. Shimotsu et al., *J. Bacteriol.*, 166, 461 (1986). A 24-mer oligonucleotide complementary to the coding strand base pairs 383–406 was endlabeled with $^{32}$P and used as the primer. The products were analyzed on a 6% polyacrylamide-urea gel.

E. Cloning of Aspartokinase II Gene

A chromosomal library of Bacillus MGA3 DNA was constructed by partial digestion of the Bacillus MGA3 chromosomal DNA with PstI followed by ligation with the PstI digested, alkaline phosphatase treated vector, pBR322. The ligation reaction was electrotransformed into *E. coli* Gif106M1 cells and tetracycline-resistant transformants selected on SOC medium. The tetracycline-resistant colonies were scraped off the SOC plates, washed twice with SSC, then plated onto M9 medium. Aspartokinase II positive clones were identified by their ability to grow on M9 medium lacking lysine, threonine, and methionine.

F. Enzymatic Assays and N-terminal Sequencing of Aspartokinase II

Aspartokinase II was assayed by measuring the amount of aspartyl-$\beta$-hydroxamate formed as described by M. J. M. Hitchcock et al., *Biochem. Biophys. Acta*, 445, 350 (1976). Determination of the apparent $K_i$ for lysine inhibition was carried out with partially purified aspartokinase II from *E. coli*/pAA8671. Cells were broken in a French press pressure cell at 16,000 psi, cell debris removed by centrifugation at 40,000×g for 1 hour, and the supernatant fractionated between 35–50% saturation with ammonium sulfate. The sample was desalted on Sephadex G-25, and apparent $K_i$ for lysine determined by varying the amount of lysine added to the assay in the presence of saturating amounts of aspartate and ATP. Determination of the N-terminal sequence of aspartokinase was carried out by automated Edman degradation at the University of Minnesota Microchemical Facility. Approximately 1 nmol of aspartokinase was run on a 14% SDS gel (U. K. Laemmuli, *Nature*, 227, 680 (1970)) to separate the $\alpha$ and $\beta$ subunits, then electroblotted onto Applied Biosystems (Forest City, Calif.) ProBlot PVDF membrane, following the manufacturer's instructions. The membrane was stained for 15 seconds with Coomassie Blue R-250 (ICN, Cleveland, Ohio), destained with 50% methanol, and the bands corresponding to the $\alpha$ and $\beta$ subunits excised and submitted for sequencing.

G. Results

1. Aspartokinase Isozymes From Bacillus sp. MGA3

Recent work in *B. subtilis* has demonstrated the existence of three aspartokinase isozymes that differ in their feedback inhibition and repression (L. M. Graves et al., cited supra). In order to determine the number of aspartokinase isozymes present in the thermophilic methylotroph B. MGA3, assays of cell extracts were carried out in the presence of lysine, threonine, or diaminopimelate alone or in combination, in accord with the methodology of J.-J. Zhang et al., *J. Bacteriol.*, 172, 701 (1990). The results of these assays are shown in Table 2, and are consistent with the presence of three isozymes; one inhibited by diaminopimelate, one inhibited by lysine alone, and one inhibited by lysine plus threonine.

TABLE 2

| Inhibition of Aspartokinase From Bacillus MGA3 by Amino Acids | |
|---|---|
| Amino Acid (5 mM) | Inhibition (%) |
| None | 100[a] |
| Lysine | 42 |
| Lysine + Threonine | 85 |
| Diaminopimelate | 12 |
| Diaminopimelate + Lysine | 55 |
| Diaminopimelate + Lysine + Threonine | 98 |

[a]Corresponds to a specific activity of 0.011 U/mg protein.

2. Cloning the Structural Gene Coding for Aspartokinase II from Bacillus sp. MGA3

Previous studies by M. Y. Chen et al., *J. Biol. Chem.*, 262, 8787 (1987) showed that the gene coding for aspartokinase II from *Bacillus subtilis* complemented *E. coli* Gif106M1, which lacks all three aspartokinase isozymes, (J. Theze et al., *J. Bacteriol.*, 117, 133 (1974)), by restoring its ability to grow on minimal medium lacking lysine, threonine and methionine. To obtain the gene coding for aspartokinase from the thermophilic methylotroph Bacillus sp. MGA3, a chromosomal library was constructed by partial PstI digestion of the MGA3 chromosome. The fragments generated were cloned into pBR322, and used to transform *E. coli* Gif106M1 to impart tetracycline resistance. After plating onto minimal medium, 40 clones were identified that restored the ability of *E. coli* Gif106M1 to grow on minimal medium lacking lysine, threonine and methionine. Analysis of 16 of these clones showed that they all shared a common 2.2 Kb PstI fragment. One of these clones, pAA8363, was used for further characterization.

In order to determine if the restored ability to grow in the absence of lysine, threonine, and methionine was due to aspartokinase, enzymatic analysis of cell extracts was carried out, with the results shown in Table 3.

TABLE 3

| Expression of Aspartokinase Activity in *E. coli* | | |
|---|---|---|
| Strain | Plasmid | Aspartokinase Activity (U/mg of protein) |
| DH5αF' | none | 0.0021[a] |
| Gif106M1 | none | 0.0002[b] |
| Gif106M1 | pBR322 | 0.0002[b] |
| Gif106M1 | pUC19cm | 0.0001[b] |
| Gif106M1 | pAA8363 | 0.022[a] |
| Gif106M1 | pAA8363 | 0.021[b] |
| Gif106M1 | PAA8802 | 0.0001[b] |

[a]Cells were grown in minimal M9 medium lacking lysine, threonine, and methionine.
[b]Cells were grown in minimal M9 medium containing lysine, threonine, and methionine.

As shown in Table 3, significant levels of aspartokinase activity were only found in the wild type *E. coli* DH5αF' and in Gif106M1 cells carrying the plasmid pAA8363. No repression of aspartokinase activity was observed when the cells were grown in the presence of 50 μg/ml of lysine, threonine, and methionine (Table 3).

Assays were performed in the presence of threonine, methionine, lysine, and diaminopimelate alone, and in combination, but only lysine was shown to inhibit enzyme activity, with an apparent $K_i$ of 100 μM.

Inactivation of the aspartokinase activity was carried out by subcloning the 2.2 Kb PstI fragment into the PstI site of pUC19cm, followed by removal of a 0.6 Kb AvaI fragment from pAA8671. The resulting clone, pAA8802, was examined for aspartokinase activity (Table 3) as well as ability to support growth of Gif106M1 on minimal medium lacking lysine, threonine, and methionine. No significant aspartokinase activity was detected, and pAA8802 would not support growth of E. coli Gif106M1 on minimal medium lacking lysine, threonine, and methionine.

The approximate location of the aspartokinase gene and control regions on the 2.2 Kb PstI fragment was determined by creating a series of unidirectional deletions, and testing each of these for their ability to support growth of Gif106M1 on a minimal medium lacking lysine, threonine, and methionine. Aspartokinase activity was lost when deletions were made 420 base pairs from the 3' end of the fragment, and 350 base pairs from the 5' end.

3. Nucleotide and Derived Amino Acid Sequences of Aspartokinase

Figure 2A:
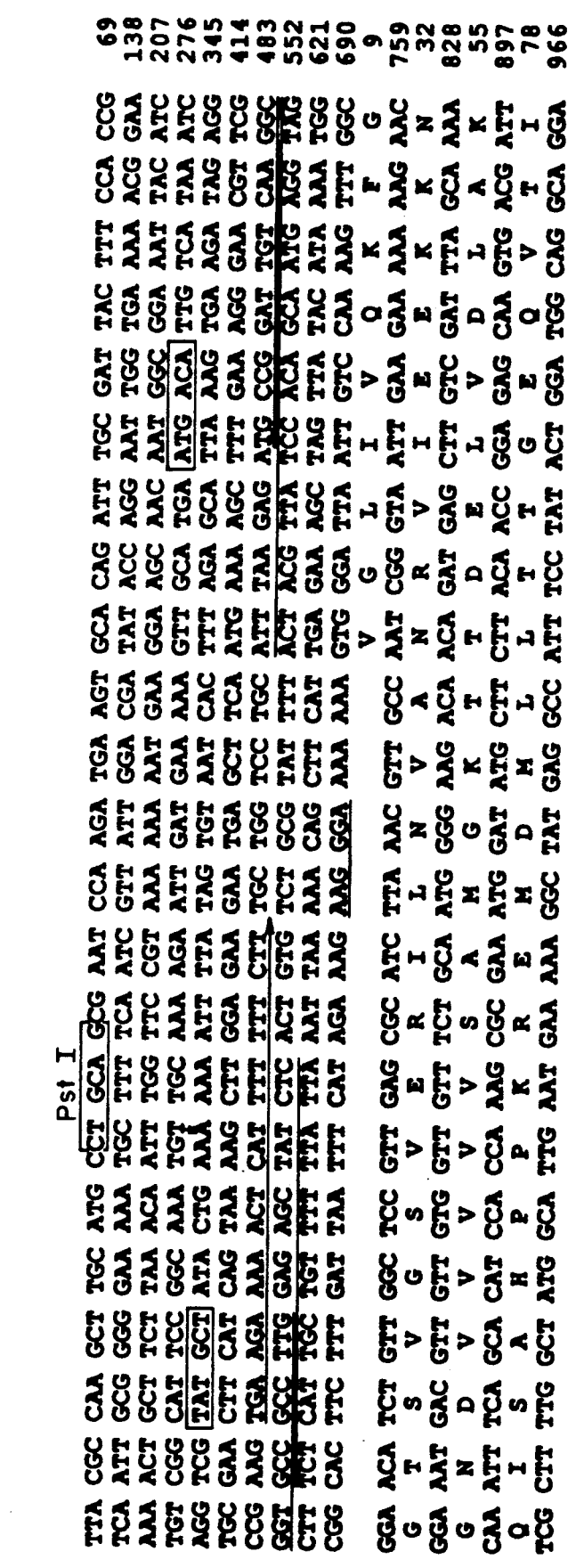
Figure 2C:
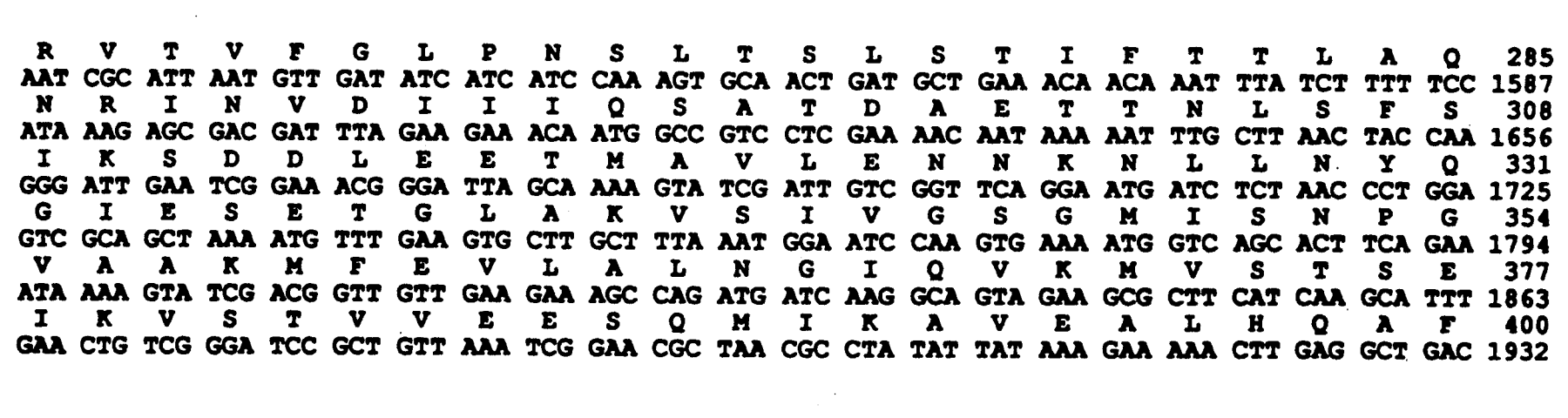

The entire 2.2 Kb PstI fragment was sequenced (FIG. 2). The nucleotide sequence (SEQ. I.D. No. 1) revealed one major open reading frame starting at base pair 790, however, there is no potential ribosome binding site preceding this possible start site. A preferred translation start site is apparent at position 664, where a GTG is preceded by a potential ribosome binding site (AAGGGA) underlined in FIG. 2). This translational start site was in complete agreement with the N-terminal amino acid sequence of the α subunit as shown in FIG. 3(A). A second start site preceded by a potential ribosome binding site, AGGAGG, was found in the same reading frame beginning at base pair 1399. This smaller open reading frame may correspond to the smaller β subunit of aspartokinase. As shown in FIG. 3(B), this second translational start site was in complete agreement with the N-terminal sequence of the β subunit. A stop codon was found at base pair 1897 resulting in predicted molecular weights for the α and β subunits of 44,313 and 17,899, respectively, and these were in good agreement with the values obtained by SDS gel electrophoresis of 45,000 and 18,000, respectively. The native molecular weight of aspartokinase was found to be 122,000 by gel filtration on Sephacryl-300, which is in good agreement with the predicted molecular weight of 124,424 for an $\alpha_2\beta_2$ tetramer.

The transcription initiation site was found by primer extension to correspond to the 'A' residue at position 297 in both the B. MGA3 and from the cloned gene in E. coli DH5αF'/pAA8671. The sequences TATGCT and ATGACA near the −10 and −35 regions correspond to a putative aspartokinase promoter (boxed in FIG. 2). Two regions of dyad symmetry with ΔG's of −18.6 and −11.1 kcal are found in the intervening sequence between transcription initiation and the translation start site (FIG. 2), and the second region contains a series of T residues following the hairpin loop typical of a rho-independent terminator. Another region of dyad symmetry with a ΔG −23.2 kcal occurs distal to the coding region, but lacks a run of T residues following the hairpin loop common to rho-independent terminators.

4. Amino Acid Sequence Comparisons of Aspartokinase

Sequence data are now available for six microbial aspartokinase isozymes, three E. coli (M. Cassan et al., J. Biol. Chem., 261 1052 (1986) (K12); M. Katinka et al., PNAS USA, 73, 5730 (1980); M. M. Zakin et al., J. Biol. Chem., 258, 3028 (1983)), the Bacillus subtilis aspartokinase II (N. Y. Chen et al., cited supra), and Saccharomyces cerevisiae (J. A. Rafalski et al., J. Biol. Chem., 263, 2146 (1988). The deduced amino acid sequence for B. MGA3 aspartokinase II (SEQ. I.D. No. 2) was compared with the proposed alignment for the B. subtilis aspartokinase II, and the three E. coli aspartokinase isozymes, the S. cerevisiae isozyme and the E. coli isozymes, the S. cerevisiae isozyme, and the E. coli isozyme. Some similarity exists between the deduced amino acid sequence of B. MGA3 aspartokinase and the B. subtilis aspartokinase II, with 76% of amino acid residues being identical. When the amino acid sequence of B. MGA3 aspartokinase is compared with the three E. coli aspartokinases and the S. cerevisiae enzyme, less similarity is found. Only 29, 23, 20, and 17% of its amino acid residues are identical to those of E. coli aspartokinase III, I, II and the S. cerevisiae aspartokinase, respectively. These findings support the assignment of MGA3 to the genus Bacillus, as discussed by F. J. Schendel et al., cited supra.

H. Discussion

Complementation of the E. coli strain Gif106M1, a mutant in all three aspartokinase isozymes, resulted in the selection of only the gene coding for aspartokinase II from B. MGA3, and neither of the genes coding for aspartokinase I or III. This is probably due to the inability of E. coli to recognize either the Bacillus promoters or Shine-Dalgarno sequences for these two isozymes (L. Band et al., DNA, 3, 17 (1984); G. Lee et al., Mol. Gen. Genet., 180, 57 (1980)). The proposed −10, TATGCT, and −35 regions, ATGACA, are similar to the compiled −10, TATAAT, and −35, TTGACA, regions from several B. subtilis genes (as reported by C. P. Moran et al., Mol. Gen. Genet., 186, 339 (1982)), and to the −10, TAAAAT, and −35, TTGTCC, regions of the B. subtilis aspartokinase II gene (N. Y. Chen et al., J. Biol. Chem., 262, 8787 (1987)). The expression of the gene coding for aspartokinase II in E. coli results from transcription initiation at the same site as in B. MGA3, and is probably due to the similarity of the −10 and −35 regions to the consensus sequences of E. coli −10, TATAAT, and −35, TTGACA, regions. In addition, the proposed Shine-Dalgarno sequences for the aspartokinase II α and β subunits, AAGGGA and AGGAGG, respectively, are both very similar to the consensus sequence, AAGGAG, of B. subtilis (C. P. Moran et al., Mol. Gen. Genet., 186, 339 (1982)). These proposed ribosome binding sites are also very similar to the E. coli consensus sequence, AGGAGG (J.-C. Patte et al., Biochem. Biophys. Acta., 136, 245 (1967)).

The large, >300 nucleotides, intervening sequence that exists between the transcription initiation and translation start sites (FIG. 2), may function in the control of aspartokinase II expression in the presence of lysine. Unlike the control sequence for the B. subtilis aspartokinase II, that contains characteristics similar to attenuators from several E. coli amino acid biosynthetic operons, as shown by R. Kolter et al., *Ann. Rev. Genet.*, 16, 113 (1982), no open reading frame preceded by a ribosome binding site that contained a lysine rich peptide was found. This also explains why attenuation of aspartokinase II was not observed when *E. coli* Gif106M1-/pAA8363 was grown in the presence of lysine (Table 3). In contrast, growth inhibition due to 22 μM lysine wa observed with *E. coli* Gif106M1 carrying a single copy plasmid containing the gene encoding the *B. subtilis* aspartokinase II (N. Y. Chen et al., *J. Biol. Chem.*, 263, 9526 (1988)). While part of this inhibition may have been due to feedback inhibition, since the aspartokinase II from *B. subtilis* had a $K_i$ 100 μM (30), it is likely that some of the growth inhibition resulted from attenuation of the aspartokinase gene.

EXAMPLE I

Mutagenesis of Aspartokinase II Gene

Site-directed mutants were constructed by in vitro second strand synthesis (Altered Sites, Promega Corp., Madison, Wis.) or by the method of T. A. Kunkel et al., *PNAS USA*, 82, 488 (1985) (Muta-Gene, Bio-Rad, Richmond, Calif.) using a mismatched oligonucleotide primer of 18-24 base pairs. A 19 base pair primer corresponding to the sequence 5'-TTTTGTTCTAATGT-TACTT was used to change the 'T' and 'G' at positions 1400 and 1401 to 'A' and 'T' respectively. This results in an amino acid change from methionine to leucine at position 246 in the protein sequence. In addition, this amino acid substitution eliminates the initiation codon for the synthesis of the β subunit resulting the synthesis of only the α subunit. Analysis of cell extracts containing this altered ($\alpha_2$) enzyme revealed that the aspartokinase activity and inhibition by lysine was essentially identical to the wild type ($\alpha_2\beta_2$) protein. This result was similar to the result obtained by Chen and Paulus, cited above.

In vitro plasmid mutagenesis was carried out using hydroxylamine as described by C. Wolf et al., *J. Bacteriol.*, 170, 4509 (1988). One μg of pAA8671 DNA was treated with 100 uL of 0.4 M hydroxylamine in 0.5 M potassium phosphate (pH 6.0) for 36 hours at 37° C. The sample was then dialyzed for 12 hours against 4 L of 1 mM EDTA (pH 7.0). Electrocompetent *E. coli* Gif106M1 cells were then transformed by electroporation with 1 ul of the dialyzed sample. The cells were allowed to recover for 1 hour in SOC, then plated onto minimal media containing 10 g/l lysine, and grown for 24 hours at 37° C. Ten colonies were selected, grown at 37° C. for 16 hours in TB containing 35 ug/ml chloramphenicol. The cells were collected by centrifugation, suspended in 50 mM potassium phosphate, and sonicated for 30 seconds to disrupt the cells. Aspartokinase II enzyme assays were preformed in the presence and absence of 100 mM lysine. Two clones, 9234 and 9236, showed decreased sensitivity to lysine with apparent $K_i$'s of 10 and 100 mM, respectively, compared to a $K_i$ of 100 uM for wild type enzyme.

The DNA coding for these altered enzymes was sequenced and only a single base pair change was found in each case. In pAA9234, a 'T' replaces the 'C' at position 1790 resulting in a single amino acid change from a serine to leucine at position 376 of the protein sequence. In pAA9236, a 'T' replaces the 'C' at position 1730 resulting in a single amino acid change from an alanine to a valine at position 356 of the protein sequence.

From the results of these mutagenesis experiments, specific mutations in the α subunit alone should result in altered lysine feedback inhibition in a wide variety of transformants.

The invention has been described with reference to various specific and preferred embodiments and techniques. However, it should be understood that many variations and modifications may be made while remaining within the spirit and scope of the invention.

---

What is claimed is:

1. An isolated DNA fragment from methylotrophic, thermotolerant Bacillus sp. MGA3 which encodes a polypeptide corresponding to the αβ dimer subunit of lysine-sensitive aspartokinase II of the methylotrophic, thermotolerant Bacillus sp. MGA3.

2. A DNA sequence corresponding to SEQ. I.D. No. 1.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 2223 base pairs
        ( B ) TYPE: Nucleic Acid
        ( C ) STRANDEDNESS: Single
        ( D ) TOPOLOGY: Linear ( i i ) MOLECULE TYPE: Genomic DNA ( v i ) ORIGINAL SOURCE: 2.2 Kb Pst frag. of PAA8671

( i x ) FEATURE:
        ( A ) NAME/KEY: Aspartokinase II Gene
        ( B ) LOCATION: 1 to 2223

( x i ) SEQUENCE DESCRIPTION: SEQ ID NO: 1:

| | | | | | | |
|---|---|---|---|---|---|---|
| TTACGCCAAG | CTTGCATGCC | TGCAGCGAAT | CCAAGATGAA | GTGCACAGAT | TTGCGATTAC | 60 |
| TTTCCACCGT | CAATTGCGGG | GGAAAAATGC | TTTTCAATCG | TTATTGGACG | ATATACCAGG | 120 |
| AATTGGTGAA | AAACGGAAAA | AACTGCTTCT | TAAACAATTT | GGTTCCGTAA | AAAAAATGAA | 180 |
| GGAAGCAACA | ATGGCGGAAA | TTACATCTGT | CGGCATTCCG | GCAAATGTTG | CAAAAGAATT | 240 |
| GATGAAAAAG | TTGCATGAAT | GACATTGTCA | TAAATCAGGT | CGTATGCTAT | ACTGAAAAAA | 300 |

```
ATTTTATAGT GTAATCACTT TAGAGCATTA AAGTGAAGAT AGAGGTGCGA ACTTCATCAG         360

TAAAAGCTTG GAGAAGAATG AGCTTCAATG AAAAGCTTTG AAAGGGAACG TTCGCCGAAG         420

TGAAGAAAAA CTCATTTTTT TCTTTGCTGG TCCTGCATTT AAGAGATGCC GGATTGTCAA         480

GGCGGTGCCG CCTTGGAGAG CTATCTCACT GTGTCTGCGT ATTTTACTAC GTTATCCACA         540

GCAATGAGGT AGCTTTCTCA TTGCTGTTTT TTATTAAATT AAAAACAGCT TCATTGAGAA         600

AGCTAGTTAT ACATAAAATG GCGGCACTTC TTTGATTAAT TTCATAGAAA GAAGGGAAAA         660

AAA GTG GGA TTA ATT GTC CAA AAG TTT GGC GGA ACA TCT GTT GGC TCC           708
    Val Gly Leu Ile Val Gln Lys Phe Gly Gly Thr Ser Val Gly Ser
    1            5                  10                    15

GTT GAG CGC ATC TTA AAC GTT GCC AAT CGG GTA ATT GAA GAA AAA AAG           756
Val Glu Arg Ile Leu Asn Val Ala Asn Arg Val Ile Glu Glu Lys Lys
              20                  25                  30

ACC GGA AAT GAC GTT GTT GTG GTT GTT TCT GCA ATG GGG AAG ACA ACA           804
Asn Gly Asn Asp Val Val Val Val Val Ser Ala Met Gly Lys Thr Thr
             35                  40                  45

GAT GAG CTT GTC GAT TTA GCA AAA CAA ATT TCA GCA CAT CCA CCA AAG           852
Asp Glu Leu Val Asp Leu Ala Lys Gln Ile Ser Ala His Pro Pro Lys
         50                  55                  60

CGC GAA ATG GAT ATG CTT CTT ACA ACC GGA GAG CAA GTG ACG ATT TCG           900
Arg Glu Met Asp Met Leu Leu Thr Thr Gly Glu Gln Val Thr Ile Ser
     65                  70                  75

CTT TTG GCT ATG GCA TTG AAT GAA AAA GGC TAT GAG GCC ATT TCC TAT           948
Leu Leu Ala Met Ala Leu Asn Glu Lys Gly Tyr Glu Ala Ile Ser Tyr
 80                  85                  90                  95

ACT GGA TGG CAG GCA GGA ATT ACA ACT GAA CCT GTT TTT GGG AAC GCG           996
Thr Gly Trp Gln Ala Gly Ile Thr Thr Glu Pro Val Phe Gly Asn Ala
                 100                 105                 110

AGA ATA TTA AAT ATC GAA ACC GAA AAA ATT CAA AAA CAG CTA AAC GAA          1044
Arg Ile Leu Asn Ile Glu Thr Glu Lys Ile Gln Lys Gln Leu Asn Glu
             115                 120                 125

GGA AAA ATT GTC GTA GTT GCC GGC TTC CAA GGT ATT GAT GAG CAC GGA          1092
Gly Lys Ile Val Val Val Ala Gly Phe Gln Gly Ile Asp Glu His Gly
         130                 135                 140

GAA ATT ACG ACT CTT GGG AGA GGC GGA TCC GAT ACT ACG GCT GTA GCA          1140
Glu Ile Thr Thr Leu Gly Arg Gly Gly Ser Asp Thr Thr Ala Val Ala
     145                 150                 155

CTT GCT GCG GCT TTG AAA GCC GAA AAA TGT GAT ATT TAC ACC GAT GTT          1188
Leu Ala Ala Ala Leu Lys Ala Glu Lys Cys Asp Ile Tyr Thr Asp Val
160                 165                 170                 175

ACT GGA GTT TTT ACT ACA GAT CCG CGC TAT GTA AAG TCG GCT AGG AAG          1236
Thr Gly Val Phe Thr Thr Asp Pro Arg Tyr Val Lys Ser Ala Arg Lys
                 180                 185                 190

CCT GCT TCT ATT TCA TAT GAT GAA ATG CTT GAA CTT GCG AAT CTT GGT          1284
Leu Ala Ser Ile Ser Tyr Asp Glu Met Leu Glu Leu Ala Asn Leu Gly
             195                 200                 205

GCG GGC GTC CTT CAT CCA AGA GCA GTA GAA TTT GCG AAA AAT TAC GGA          1332
Ala Gly Val Leu His Pro Arg Ala Val Glu Phe Ala Lys Asn Tyr Gly
         210                 215                 220

ATT ACT TTG GAG GTG CGC TCC AGT ATG GAA CGA GAA GAA GGG ACG ATC          1380
Ile Thr Leu Glu Val Arg Ser Ser Met Glu Arg Glu Glu Gly Thr Ile
     225                 230                 235

ATT GAG GAG GAA GTA ACA ATG GAA CAA AAT CTT GTT GTC CGG GGA GTA          1428
Ile Glu Glu Glu Val Thr Met Glu Gln Asn Leu Val Val Arg Gly Val
240                 245                 250                 255

GCT TTT GAA GAT GAA ATC ACT CGA GTA ACA GTT TTT GGA TTG CCA AAC          1476
Ala Phe Glu Asp Glu Ile Thr Arg Val Thr Val Phe Gly Leu Pro Asn
                 260                 265                 270

TCA TTA ACG AGT TTA TCT ACT ATT TTT ACG ACA CTT GCT CAA AAT CGC          1524
```

```
           Ser  Leu  Thr  Ser  Leu  Ser  Thr  Ile  Phe  Thr  Thr  Leu  Ala  Gln  Asn  Arg
                          275                      280                     285

ATT  AAT  GTT  GAT  ATC  ATC  ATC  CAA  AGT  GCA  ACT  GAT  GCT  GAA  ACA  ACA              1572
           Ile  Asn  Val  Asp  Ile  Ile  Ile  Gln  Ser  Ala  Thr  Asp  Ala  Glu  Thr  Thr
                          290                      295                     300

AAT  TTA  TCT  TTT  TCC  ATA  AAG  AGC  GAC  GAT  TTA  GAA  GAA  ACA  ATG  GCC              1620
           Asn  Leu  Ser  Phe  Ser  Ile  Lys  Ser  Asp  Asp  Leu  Glu  Glu  Thr  Met  Ala
                     305                      310                     315

GTC  CTC  GAA  AAC  AAT  AAA  AAT  TTG  CTT  AAC  TAC  CAA  GGG  ATT  GAA  TCG              1668
           Val  Leu  Glu  Asn  Asn  Lys  Asn  Leu  Leu  Asn  Tyr  Gln  Gly  Ile  Glu  Ser
           320                      325                     330                     335

GAA  ACG  GGA  TTA  GCA  AAA  GTA  TCG  ATT  GTC  GGT  TCA  GGA  ATG  ATC  TCT              1716
           Glu  Thr  Gly  Leu  Ala  Lys  Val  Ser  Ile  Val  Gly  Ser  Gly  Met  Ile  Ser
                               340                      345                     350

AAC  CCT  GGA  GTC  GCA  GCT  AAA  ATG  TTT  GAA  GTG  CTT  GCT  TTA  AAT  GGA              1764
           Asn  Pro  Gly  Val  Ala  Ala  Lys  Met  Phe  Glu  Val  Leu  Ala  Leu  Asn  Gly
                          355                      360                     365

ATC  CAA  GTG  AAA  ATG  GTC  AGC  ACT  TCA  GAA  ATA  AAA  GTA  TCG  ACG  GTT              1812
           Ile  Gln  Val  Lys  Met  Val  Ser  Thr  Ser  Glu  Ile  Lys  Val  Ser  Thr  Val
                     370                      375                     380

GTT  GAA  GAA  AGC  CAG  ATG  ATC  AAG  GCA  GTA  GAA  GCG  CTT  CAT  CAA  GCA              1860
           Val  Glu  Glu  Ser  Gln  Met  Ile  Lys  Ala  Val  Glu  Ala  Leu  His  Gln  Ala
           385                      390                     395

TTT  GAA  CTG  TCG  GGA  TCC  GCT  GTT  AAA  TCG  GAA  CGC  TAACGC  CTAT                    1906
           Phe  Glu  Leu  Ser  Gly  Ser  Ala  Val  Lys  Ser  Glu  Arg
           400                      405                     410

ATTATAAAGA  AAAACTTGAG  GCTGACCCAT  AAGGTCCTGG  CTCGCGTTTG  CAGTTACTAA                      1966

ATATTGTAGA  AACAGTAATC  ATGTTTTTA   ATATTTAGTA  ACTGAGAGTG  CCTGGCTCTT                      2026

AGTCTTGGGT  CAGCCTTTAT  CCATAAATCA  TGGCTTTACG  ACGTCTTTTT  TGTCCCACTT                      2086

AACCGTTATT  AGCACCTTTG  ATCCCTTTTT  ACGAGGGTGT  TCAAACGCTT  CAGCAATTAC                      2146

TTTTTTTTGC  TGTTCAATTT  GCTGGGCAAT  AAATCCCGCT  TCCAACTGAA  AAGAGATATC                      2206

TTTTTTTGAC  TGCAGGT                                                                         2223

( 2 ) INFORMATION FOR SEQ ID NO: 2:

( i ) SEQUENCE CHARACTERISTICS:
                 ( A ) LENGTH: 411 amino acids
                 ( B ) TYPE: Amino Acid
                 ( D ) TOPOLOGY: Linear ( i i ) MOLECULE TYPE: Polypeptide ( i x ) FEATURE:
                 ( A ) NAME/KEY: Aspartokinase II dimer subunit
                 ( B ) LOCATION: 1 to 411

( x i ) SEQUENCE DESCRIPTION: SEQ ID NO: 2:

Val  Gly  Leu  Ile  Val  Gln  Lys  Phe  Gly  Gly  Thr  Ser  Val  Gly  Ser  Val
           1                   5                    10                      15

Glu  Arg  Ile  Leu  Asn  Val  Ala  Asn  Arg  Val  Ile  Glu  Glu  Lys  Lys  Asn
                          20                       25                      30

Gly  Asn  Asp  Val  Val  Val  Val  Ser  Ala  Met  Gly  Lys  Thr  Thr  Asp
                     35                        40                     45

Glu  Leu  Val  Asp  Leu  Ala  Lys  Gln  Ile  Ser  Ala  His  Pro  Pro  Lys  Arg
                50                       55                      60

Glu  Met  Asp  Met  Leu  Leu  Thr  Thr  Gly  Glu  Gln  Val  Thr  Ile  Ser  Leu
           65                       70                      75                          80

Leu  Ala  Met  Ala  Leu  Asn  Glu  Lys  Gly  Tyr  Glu  Ala  Ile  Ser  Tyr  Thr
                               85                       90                          95
```

-continued

| | | | | | | | | | | | | | |
|---|---|---|---|---|---|---|---|---|---|---|---|---|---|
| Gly | Trp | Gln | Ala 100 | Gly | Ile | Thr | Thr | Glu 105 | Pro | Val | Phe | Gly | Asn Ala Arg 110 |
| Ile | Leu | Asn 115 | Ile | Glu | Thr | Glu | Lys 120 | Ile | Gln | Lys | Gln | Leu 125 | Asn Glu Gly |
| Lys | Ile 130 | Val | Val | Val | Ala | Gly 135 | Phe | Gln | Gly | Ile | Asp 140 | Glu | His Gly Glu |
| Ile 145 | Thr | Thr | Leu | Gly | Arg 150 | Gly | Gly | Ser | Asp | Thr 155 | Thr | Ala | Val Ala Leu 160 |
| Ala | Ala | Ala | Leu | Lys 165 | Ala | Glu | Lys | Cys | Asp 170 | Ile | Tyr | Thr | Asp Val Thr 175 |
| Gly | Val | Phe | Thr 180 | Thr | Asp | Pro | Arg | Tyr 185 | Val | Lys | Ser | Ala | Arg Lys Leu 190 |
| Ala | Ser | Ile 195 | Ser | Tyr | Asp | Glu | Met 200 | Leu | Glu | Leu | Ala | Asn 205 | Leu Gly Ala |
| Gly | Val 210 | Leu | His | Pro | Arg | Ala 215 | Val | Glu | Phe | Ala | Lys 220 | Asn | Tyr Gly Ile |
| Thr 225 | Leu | Glu | Val | Arg | Ser 230 | Ser | Met | Glu | Arg | Glu 235 | Glu | Gly | Thr Ile Ile 240 |
| Glu | Glu | Glu | Val | Thr 245 | Met | Glu | Gln | Asn | Leu 250 | Val | Val | Arg | Gly Val Ala 255 |
| Phe | Glu | Asp | Glu 260 | Ile | Thr | Arg | Val | Thr 265 | Val | Phe | Gly | Leu | Pro Asn Ser 270 |
| Leu | Thr | Ser 275 | Leu | Ser | Thr | Ile | Phe 280 | Thr | Thr | Leu | Ala | Gln 285 | Asn Arg Ile |
| Asn | Val 290 | Asp | Ile | Ile | Ile | Gln 295 | Ser | Ala | Thr | Asp | Ala 300 | Glu | Thr Thr Asn |
| Leu 305 | Ser | Phe | Ser | Ile | Lys 310 | Ser | Asp | Asp | Leu | Glu 315 | Thr | Met | Ala Val 320 |
| Leu | Glu | Asn | Asn | Lys 325 | Asn | Leu | Leu | Asn | Tyr 330 | Gln | Gly | Ile | Glu Ser Glu 335 |
| Thr | Gly | Leu | Ala 340 | Lys | Val | Ser | Ile | Val 345 | Gly | Ser | Gly | Met | Ile Ser Asn 350 |
| Pro | Gly | Val 355 | Ala | Ala | Lys | Met | Phe 360 | Glu | Val | Leu | Ala | Leu 365 | Asn Gly Ile |
| Gln | Val 370 | Lys | Met | Val | Ser | Thr 375 | Ser | Glu | Ile | Lys | Val 380 | Ser | Thr Val Val |
| Glu 385 | Glu | Ser | Gln | Met | Ile 390 | Lys | Ala | Val | Glu | Ala 395 | Leu | His | Gln Ala Phe 400 |
| Glu | Leu | Ser | Gly | Ser 405 | Ala | Val | Lys | Ser | Glu 410 | Arg | | | |